United States Patent [19]

Vietti

[11] 4,376,208

[45] Mar. 8, 1983

[54] HYDROFORMYLATION OF DIHYDROFURAN

[75] Inventor: David E. Vietti, Cary, Ill.

[73] Assignee: The Quaker Oats Company, Chicago, Ill.

[21] Appl. No.: 293,533

[22] Filed: Aug. 17, 1981

[51] Int. Cl.³ .................. C07D 307/12; C07D 307/20
[52] U.S. Cl. .................................... 549/478; 549/475; 549/483; 549/489
[58] Field of Search ..................... 260/347.8, 345.9 R; 549/475, 478, 483, 489

[56] References Cited

PUBLICATIONS

Wender et al., Organic Syntheses via Metal Carbonyls, Wiley & Sons, Inc., (New York), 1977, pp. 46–197.
Pittman et al., JACS, vol. 97, No. 7, (1975), pp. 1742–1754.

Primary Examiner—Richard Raymond
Attorney, Agent, or Firm—Gerald T. Shekleton

[57] ABSTRACT

A hydroformylation process is disclosed in which unsaturated cyclic ethers, such as unsaturated furans can be hydroformylated in good yield and under relatively mild conditions.

3 Claims, No Drawings

HYDROFORMYLATION OF DIHYDROFURAN

BACKGROUND OF THE INVENTION

This invention relates in general to the oxonation or hydroformylation of unsaturated cyclic ethers and in particular to the hydroformylation of dihydrofuran derivatives.

Hydroformylation of olefins has been known since 1938 and was commercialized in the early 1950's as a method of producing alcohols by reducing the aldehydes formed through the hydroformylation reaction. In this reaction hydrogen and carbon monoxide are added across an olefinic bond to produce aldehydes containing one more carbon atom than the olefin.

In the hydroformylation reaction, catalysis of the reactants can be homogeneously carried out through carbonyls of group VIII metals, such as iron, cobalt, nickel, ruthenium, rhodium, palladium, osmium, iridium & platinum. Although the exact hydroformylation reaction mechanism is not completely understood, it is now generally agreed that it involves alkyl and acyl metal carbonyls as intermediates. Further, it is reasonably well established that "carbonyl insertion", the migration of a carbon monoxide ligand in the carbonyl to a position between the alkyl group and the metal atom takes place.

In spite of the great deal of study and the commercial success of the hydroformylation reactions with olefins for forming aldehydes and subsequently alcohols, the preparation of aldehydes in good yield from the hydroformylation of unsaturated cyclic ethers such dihydrofurans has not been reported.

Furans have reportedly been hydroformylated to hydroxymethyl tetrahydrofurans in modest yield using $Co_2 (CO)_8$ and dihydropyrans have been hydroformylated using $Co_2 (CO)_8$ to hydroxymethyl tetrahydropyrans in good yield. However, in either case only low yields of the intermediate aldehydes could be isolated. In the hydroformylation reaction, rhodium complexes (e.g., Rh H (CO) (PPh$_3$)$_3$ and Rh Cl (CO) (PPh$_3$)$_2$) have been found to be more active hydroformylation catalysts than cobalt compounds.

SUMMARY OF THE INVENTION

Therefore an object of the subject invention is the hydroformylation of unsaturated cyclic ethers.

A further object of the subject invention is the use of rhodium catalysts in the hydroformylation of dihydrofurans.

Yet another object of the subject invention is the hydroformylation of 2,5 dihydrofuran by a rhodium catalyst under pressure to give increased yields of tetrahydrofuran-3-carbaldehyde.

These and other objects are obtained in accordance with the present invention wherein there is provided a method of hydroformylating unsaturated cyclic ethers utilizing rhodium catalysts in general and specifically Rh Cl (CO) PPh$_3$)$_2$+Et$_3$N and Rh H (CO) (PPh$_3$)$_3$. The hydroformylation of 2,3 and 2,5 dihydrofuran derivatives with such catalysts produce the aldehydes tetrahydrofuran-3-carbaldehyde and tetrahydrofuran-2-carbaldehyde rapidly and in good yield under mild conditions.

DESCRIPTION OF PREFERRED EMBODIMENT

As herein before set forth, the present invention is concerned with a process for preparing predominantly aldehydes, with the process being effected by the hydroformylation of unsaturated cyclic ethers with carbon monoxide and hydrogen in the presence of a catalyst comprising a rhodium containing compound.

In addition to 2,3 dihydrofuran, 2,5 dihydrofuran and their derivatives, substituted dihydrofurans such as

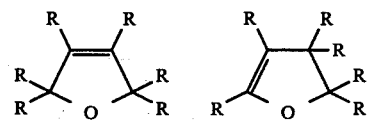

where R groups may be the same or different and may be hydrogen, alkyl, aryl, arylalkyl, alkylaryl, hydroxy, alkoxy, aryloxy, acyloxy, or substituted alkyl, aryl, alkylaryl, or arylalkyl groups, etc., may also be hydroformylated according to the subject invention.

The reaction, according to the subject invention, takes place under conditions which include a temperature in the range of from about 25° C. to about 180° C. and preferably in a range of from about 85° C. to about 95° C. In addition another reaction condition involves pressure with the total pressure ranging from atmospheric to about 1000 psig or more, and the partial pressure of $H_2/CO$ ranging from 10:1 to 1:10, but will normally be from about 3:1 to about 1:3 with about 1:1 ratio being preferred.

The catalytic compositions of matter which are used in the process of this subject invention comprise any known hydroformylation rhodium-containing catalysts, such as, rhodium carbonyls of the formula $(Rh (CO)_3)_x$, e.g., $Rh_4(CO)_{12}$ and $Rh_6(CO)_{18}$. It is also contemplated within the scope of the subject invention that phosphoric containing ligands such as a trialkylphosphine may be present as one component of the complexed rhodium catalyst. The hydrocarbonyl components need not necessarily be the same as suitable tertiary organophosphine ligands comprise the mixed phosphine where different members of the group are comprised of alkyl, aryls, aryl alkyl and alkyl aryls. A particularly preferred group of catalysts would include the arylphosphine rhodium carbonyl complexes which include the complexes of Rh Cl (CO) (PPh$_3$)$_2$ and RhH (CO) (PPh$_3$)$_3$. Specific examples of suitable catalysts of the above-defined classes comprise complexes formed in situ between rhodium, carbon monoxide and one of the following tertiary organophosphines such as trimethyl phosphine, triethyl phosphine, tris-n-butyl phosphine, triamyl phosphine, trihexyl phosphine, tripropyl phosphine, trinonyl phosphine, tridecyl phosphine, tri-n-butyloctadecyl phosphine, dimethylethyl phosphine, diamylethyl phosphine, ethyl-bis-(beta-phenyl ethyl) phosphine, dimethylcyclopentyl phosphine, diphenylbenzyl phosphine, diethylphenyl phosphine, triphenyl phosphine, etc. Chelating diphosphines, such as, (+)-2,3-O-Isopropylidene-2,3-dihydroxy-1,4-bis (diphenylphosphino) butane (DIOP), 1,1'-Bis (diphenylphosphino) ferrocene (BDPF), bisdiphenyl phosphino ethane, bisdiphenyl phosphino propane, bisdiphenyl phosphino butane are also suitable for catalyst components useful with the subject invention.

In addition polymer bound rhodium phosphine complexes have been used in hydroformylations and may be utilized in hydroformylations of the subject invention. Examples of such polymer bound hydroformylation catalysts may be found in Pittman and Smith, Journal of the American Chemical Society 97:7, Apr. 2, 1975.

The process of the subject invention may be effected in any suitable manner and may comprise either a batch or a continuous type operation. For example, when a batch type operation is employed, the reactants, comprising the unsaturated compounds, carbon monoxide and hydrogen, are placed in an appropriate reaction vessel, such as an autoclave apparatus along with a catalyst comprising the rhodium containing compound. The autoclave is sealed, heated to the desired operating temperature and maintained thereat for a predetermined residence time. At the end of this time, which may comprise on or about 0.5 up to 5 hours or more in duration, the heating is discontinued, the autoclave is allowed to return to room temperature, and vented. The reaction mixture is then recovered, separated from the catalyst and subject to conventional means of purification and separation, including washing, drying, extraction, evaporation, fractional distillation, etc., whereby the aldehyde may be recovered.

As stated, it is also contemplated within the scope of the subject invention that the hydroformylation process for obtaining the desired aldehydes may be effected in a continuous manner of operation. When such a type of operation is employed, the reactants comprising the unsaturated compounds are continuously charged to the hydroformylation zone containing the rhodium containing compound with the hydroformylation zone being maintained at the proper operating conditions of temperature and pressure by heat and the admission of the requisite quantities of carbon monoxide, hydrogen and any substantially inert gas which may be required for effecting the hydroformylation reaction. After completion of the desired residence time, the reactor effluent is continuously withdrawn and subjected to conventional means of separation. By such separation means the desired aldehyde can be recovered and any unreacted starting material comprising the unreacted unsaturated compound carbon monoxide or hydrogen can be recycled to the reaction zone to form a portion of the feed stock or gaseous hydrogen or carbon monoxide stream. The rhodium containing material may be recovered from the reaction mixture by various methods known to the art and regenerated to form fresh catalysts.

It is contemplated within the scope of the process of the present invention that the hydroformylation may be effected in an inert organic aromatic media as exemplified by benzene, toluene, xylene, etc.

The following examples are given to illustrate the process of the subject invention. However such examples are not intended to limit the scope of the invention as set forth therein:

EXAMPLE I

The rhodium complex (0.2–0.3 m mole) was dissolved in 30–50 ml of degassed toluene with gentle warming under nitrogen atmosphere. When chlorocarbonytris (triphenylphosphine) rhodium (I) was used as a catalyst, 1 ml of triethylamine was added and when ligands such as (+)-2,3-O-Isopropylidene-2,3-dihydroxy-1,4-bis (diphenylphosphino) butane (DIOP) or 1,1'-Bis (diphenylphosphino) ferrocene (BDPF) were used they were added at this point. The catalyst solution and 15 ml of the dihydrofuran were placed in a 300 cc stainless steel autoclave (Autoclave Engineers, Inc.). The autoclave was flushed with carbon monoxide, pressurized with carbon monoxide then with hydrogen. The solution was stirred and the autoclave heated with an electric furnace to the desired temperature. The temperature was maintained within ±3° by means of a temperature controller which controlled the autoclave heater and a solenoid which opened or closed a valve allowing water to flow through the autoclave cooling coils. The progress of the reaction was followed by the rate of pressure drop in the autoclave. When the pressure declined at a very low rate, the autoclave was then cooled and flushed with nitrogen. The solution was removed through a sampling tube and analyzed by Gas-Liquid Chromatography (GLC). The products were isolated by simple distillation from the reaction medium. After removal of solvent the aldehydes were collected as a colorless liquid at 60°–70° C., 28–30 mm. The products were purified by preparative GLC and identified by their $^1$H NMR and IR spectra as tetrahydrofuran-2-carbaldehyde and tetrahydrofuran-3-carbaldehyde. The results are summarized in Table 1.

TABLE 1

Hydroformylation of Dihydrofuran

| Substrate | Catalyst | (m moles) | Temp. °C. | Initial[b] Pressure (psig) | Final[b] Pressure (psig) | Time (hours) | Conversion[c] % | Products[c] (%) CHO (2-) | Products[c] (%) CHO (3-) |
|---|---|---|---|---|---|---|---|---|---|
| 2,3 DHF[a] | RhCl (CO) (PPh$_3$)$_2$ + Triethylamine | (0.3) (7.2) | 95 | 870 | 430 | 0.5 | 95 | 35 | 60 |
| 2,3 DHF | Rh$_4$ CO$_{12}$ | (0.15) | 120 | 1000 | 600 | 3.0 | 70 | 50 | 20 |
| 2,3 DHF | Rh H(CO) (PPh$_3$)$_3$ + DIOP[d] | (0.09) (0.35) | 90 | 850 | 500 | 2 | 75 | 5 | 70 |
| 2,3 DHF | Rh H(CO) (PPh$_3$)$_3$ + BDPF[e] | (0.10) (0.15) | 95 | 950 | 550 | 2 | 54 | 13 | 41 |
| 2,3 DHF | Rh Cl (CO) (PPh$_3$)$_2$ Polymer Bound[f] | (0.05)[f] | 100 | 950 | 550 | 7 | 60 | 34 | 26 |
| 2,5 DHF[g] | RhH (CO) (PPh$_3$)$_3$ | (0.2) | 85 | 750 | 470 | 1 | 100 | 5 | 95 |

[a]DHF = Dihydrofuran
[b]Values given are total pressure (H$_2$/CO = 1) at reaction temperature.
[c]Product yield and percent DHF conversion were estimated by GLC without use of internal standards.
[d]DIOP = (+)-2,3-O—Isopropylidene-2,3-dihydroxy-1,4-bis(diphenylphosphino) butane
[e]BDPF = 1,1'-Bis(diphenylphosphino) ferocene
[f]Polymer bound Wilkinson's Catalyst on styrene divenylbenzene copolymer linked (Strem Chemicals Inc.). Only the sample size used contained 0.05m moles of rhodium.
[g]Only 10 ml of 2,5 DHF was used compared to 15 ml of 2,3 DHP used in the other experiments.

EXAMPLE II

The autoclave was charged with Rh Cl (CO) (PPh$_3$)$_2$ (200 mg, 0.3 m mole), 1 ml of triethylamine, and 20 ml (0.14 mole) of 2,5 dimethoxy-2,5-dihydrofuran in 50 ml of degassed toluene. The hydroformylation was carried out as before at 90° C. The initial pressure was 850 psig (CO/H$_2$=1) at ambient temperature. The pressure reached 890 psig at 75° C. then dropped rapidly. After 10 min. at 90° C. the pressure was 470 psig and no further decrease was observed. An additional 20 ml of 2,5 dihydrofuran was added to the autoclave and hydroformylated in the same manner. The solution was removed from the autoclave and distilled under reduced pressure. After toluene was removed, the product was collected as a colorless liquid at 76°–78° C., 5 mm in 80% yield. The product was identified as a mixture of stereoisomers of 3-formyl-2,5-dimethoxytetrahydrofuran: $^1$H NMR (60 MH$_z$, CDCl$_3$) δ9.5–9.7 (m,1H,CHO), 5.1–5.5 (m,2H,H$_2$,H$_5$), 3.4–3.6 (m,6H,OCH$_3$), 3.3–3.4 (m,1H, H$_3$), 2.1–2.7 (m,2H,H$_4$). The Gas-Liquid Chromatography (GLC) analysis showed four major product peaks. The mass spectra of the four stereoisomeric products were identical exhibiting prominent ions at m/e 159 (M-1), 129, 100, 85, 71, 69, 58, 45, 41.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

I claim:

1. A method for the hydroformylation of a a dihydrofuran comprising the steps of:
   (a) reacting said dihydrofuran in a reaction vessel with carbon monoxide and hydrogen in the presence of a catalyst,
   (b) said catalyst comprising a rhodium complex selected from the group of rhodium carbonyls, aryl phosphine rhodium carbonyl complexes and polymer bound rhodium phosphine complexes,
   (c) causing said reaction to occur at a temperature in the range of from about 25° C. to 180° C. and at a pressure of from about 1000 psig,
   (d) allowing said reaction to continue for a period of time sufficient to hydroformylate said dihydrofuran reactants,
   (e) thereby producing aldehydic tetrahydrofurans having one more carbon atom than the cyclic reactants.

2. The method of claim 1 wherein said carbon monoxide and hydrogen are introduced into said reaction vessel with partial pressures in ratios of carbon monoxide to hydrogen of from about 10:1 to about 1:10.

3. The method of claim 1 wherein said carbon monoxide and hydrogen are introduced into said reaction vessel with partial pressures approximately equal.

* * * * *